United States Patent [19]

Porter et al.

[11] Patent Number: 4,806,467
[45] Date of Patent: Feb. 21, 1989

[54] METHOD FOR THE DETECTION OF EQUINE INFECTIOUS ANEMIA AND OTHER RETROVIRUS INFECTIONS USING A COMPETITIVE ENZYME-LINKED IMMUNOABSORBENT ASSAY AND REAGENTS USEFUL IN THE SAME

[75] Inventors: James P. Porter, Oakland, Calif.; Tatsuo Matsushita; Lyndal K. Hesterberg, both of Fort Collins, Colo.

[73] Assignee: Fermenta Animal Health Company, Kansas City, Mo.

[21] Appl. No.: 789,910

[22] Filed: Oct. 21, 1985

[51] Int. Cl.$^4$ .................... G01N 33/53; G01N 33/543
[52] U.S. Cl. ..................................... 435/7; 435/172.1; 435/172.2; 436/518; 436/527; 436/528; 436/529; 436/531; 436/536; 436/542; 436/543; 436/548
[58] Field of Search ................ 435/7, 172.2; 436/518, 436/527, 528, 529, 531, 536, 542, 543, 548

[56] References Cited
PUBLICATIONS

Chem. Abst. 10th Collect. Index, vol. 86-95 (1977-1981) General Subjects, pp. 24549GS and 24588GS-24589GS.
Maggio-Enzyme-Immunoassay (1980), CRC Press, pp. 106-107.
Matsushita et al.-Am. Assn. Vet. Lab. Diag. 27th Annual Proceed. (1984) pp. 27-34.

*Primary Examiner*—Sam Rosen
*Attorney, Agent, or Firm*—Sughrue, Mion, Zinn, Macpeak, and Seas

[57] ABSTRACT

The present invention relates to a method of detecting either antibody or antigen in the serum of horses infected with equine infectious anemia using a competitive enzyme-linked immunoabsorbent assay technique and reagents useful in such an assay. The competitive enzyme-linked immunoabsorbent assay incorporates a purified virus antigen conjugate and a monoclonal antibody specific for the virus antigen as both the reacting and competing components. Alternatively, the competitive enzyme-linked immunoabsorbent assay incorporates a purified virus antigen and a monoclonal antibody conjugate specific for the viral antigen as both reacting and competing components. This invention also relates to detecting antigen and antibody found in other retrovirus infections such as Acquired Immunodeficiency Syndrome in humans.

29 Claims, No Drawings

METHOD FOR THE DETECTION OF EQUINE INFECTIOUS ANEMIA AND OTHER RETROVIRUS INFECTIONS USING A COMPETITIVE ENZYME-LINKED IMMUNOABSORBENT ASSAY AND REAGENTS USEFUL IN THE SAME

FIELD OF THE INVENTION

The present invention relates to a method of detecting either antibody or antigen in the serum of horses infected with equine infectious anemia using a competitive enzyme-linked immunoabsorbent assay (hereinafter "CELISA") and reagents useful in such a method. The CELISA incorporates a purified virus antigen conjugate and a monoclonal antibody specific for the virus antigen as both the reacting and competing components. Alternatively, the CELISA incorporates a purified virus antigen and a monoclonal antibody conjugate specific for the virus antigen as both reacting and competing components. This invention also relates to a method of detecting virus specific antigen and antibody specific thereto found in other retrovirus infections such as Acquired Immunodeficiency Syndrome (hereinafter "AIDS") in humans.

BACKGROUND OF THE INVENTION (I) Equine Infectious Anemia

Equine infectious anemia (hereinafter "EIA") is a disease that primarily affects horses and ponies and is commonly known as swamp fever. EIA or swamp fever is a progressive disease of horses and other Equidae. The disease is caused by a virus in the lentivirus subfamily of the retrovirus family. The EIA virus infection results in a chronic disease whose main pathology is the immune-mediated destruction of red blood cells. The persistent disease can progress through acute, subacute, chronic and inapparent forms. The virus persists and escapes destruction by the host animal by hiding in macrophages and by mutating into variant strains. Diagnosis is the major means for the prevention and control of the disease because there is no vaccine or cure for EIA. The disease has been controlled in the United States by a federally regulated test and isolation/slaughter program. The official test for this federally regulated program is the Coggins agar gel immunodiffusion test (hereinafter "AGID test") (see: U.S. Pat. Nos. 3,929,982 and 3,932,601). The object of this test is to detect antibody against the EIA virus because antibodies against the virus can be detected more easily over a longer period of time than can the virus itself. The EIA virus antigen forms a visible precipitin line with antibodies specific for EIA virus. However, U.S. Pat. Nos. 3,929,982 and 3,932,601 do not identify the specific virus antigens that are involved in the test.

The EIA virus contains four major non-glycosylated-proteins designated as p26, p15, p11 and p9, and two glycoproteins designated as gp90 and gp45 see: Montelaro, C. J., et al, *J. Virol.* 42:1029-1038 (1982)). p26 is known as the core antigen and is the predominant protein found in the core of EIA virus. The Coggins AGID test detects mostly p26-specific antibody. The Coggins AGID test is effective as a diagnostic tool because p26 does not mutate and antibody to p26 persists in the blood of horses throughout the course of the disease and for up to seven years. In contrast, systems which directly detect virus antigen have not been developed because of the transient viremia (see: Issel, C. J., et al, *J. Am. Vet. Med. Assoc.*, 1974:727 (1979)).

A problem in the Coggins AGID test is the appearance of nonspecific precipitin lines that are formed by antibodies against contaminating antigens (i.e. non-EIA antigens) in the manufacture of virus preparations. Recently, this problem has been solved by using novel techniques to prepare purified EIA virus antigen (see: U.S. patent application Ser. No. 607,895, filed May 7, 1984). This new version of the AGID test has been licensed and is currently manufactured by TechAmerica Diagnostics under the DiaSystems-EIA label. However, this new AGID test and the Coggins AGID test are disadvantageous for the following reasons: (1) The formation of clearly visible precipitin lines takes 24-48 hours; (2) The performance of the AGID test is labor intensive requiring the laboratory technician to make agar plates, prepare seven-hole patterns on the plates, and perform laborious visual interpretations of the results; (3) The AGID tests detect virus-antigen-specific antibody and cannot directly detect virus antigen. As a result, the early viremia associated with this disease cannot be detected by these AGID tests even though the horse may show early EIA symptoms with no antibody response; and (4) The sensitivity of these AGID tests is limited to antibody concentrations which either form precipitin lines or cause bends in the reference serum lines.

(II) Acquired Immune Deficiency Syndrome

The human T-cell leukemia viruses (hereinafter "HTLV") are structurally similar to the EIA virus and contain a single stranded RNA genome and a RNA-dependent DNA polymerase (reverse transcriptase). Both HTLV and the EIA virus are part of the family retroviridae and are commonly referred to as retroviruses. The HTLV-III virus has been isolated and causally linked to AIDS (see: Popovic, M., et al, *Science* 224:497-500 (1984); Gallo, R. C., et al, *Science* 224:500-503 (1984); Schupbach, J., et al, *Science* 224:503-505 (1984); Sarngadharan, M. G., et al, *Science* 224:506-508 (1984)) and appears to be identical to the lymphadenopathy-associated virus (hereinafter "LAV") which has also been linked to AIDS (see: Montagnier, L., et al, In *Human T-Cell Leukemia/Lymphoma Virus,* Gallo, R. C., Essex, M., and Gross, L., eds., Cold Spring Harbor, N.Y.; Cold Spring Harbor Laboratory), pp. 363-370(1984)). The morphology of HTLV-III resembles EIA virus and visna-virus (both lentiviruses) more than HTLV-I or HTLV-II (see: Gonda, M. A., et al, *Science* 227:173-177 (1985)). HTLV-III has at least three glycosylated proteins designated as gp160, gp120 and gp41 (gp46) and three nonglycosylated proteins designated as p70, p55 and p24 (Robey, W. G., et al, *Science* 228:593-595 (1985)). p24 is known as the core antigen and is the major structural protein found in the mature virion core of HTLV-III. p24 of HTLV-III corresponds to p26 of EIA, the major structural protein of the EIA virus core.

The similarity of LAV and EIA virus morphology has been independently observed (see: Brun-Vezinet, F., et al, *Science* 226:453-456 (1984)). In addition, sera from EIA virus-infected horses precipitate the p24 core protein of LAV (see: Montagnier, L., et al, *Science* 225:63-66 (1984) and Montagnier, L. et al, In *Human T-Cell Leukemia/Lymphoma Virus,* Gallo, R. C., Essex, M., and Gross, L., eds. (Cold Spring Harbor, N.Y.; Cold Spring Harbor Laboratory), pp. 363-370 (1984)). Thus, it has been demonstrated that antigenic cross-reactivity between EIA virus and HTLV-III exists (see: Casey, J. M., et al, *J. Virol.* 55:417–423 (1985)). Hence, morphological and antigenic similarities exist between HTVL-III (LAV) and EIA virus. Therefore, CELISA methods developed for EIA antibody and antigen detection are believed to be effective for AIDS antibody and antigen detection.

(III) Other Retroviruses

As discussed above, retroviruses include the subfamily lentivirus. Specific lentiviruses include progressive pneumonia virus (see: Kennedy, R. C., et al, *Virology.* 35:483 (1968)), and caprine arteritis and encephalitis virus. There is limited immunological cross-reactivity between EIA virus and these viruses (see: Brahic, M., et al in *Comparative Diagnosis of Viral Diseases*, Vol. 14, Kurstak, E., and Kurstak, C., eds., pp. 619–643, Academic Press, New York, (1981)). It is believed that this cross-reactivity involves the core antigen of these viruses. Thus, CELISA of the present invention directed to measuring the core antigen of EIA and antibodies specific thereto is also believed to be applicable to other retroviruses. In any event, the core antigen of these other retroviruses can also be purified and employed in the present invention to measure the presence thereof in test samples as disclosed in more detail below.

(IV) Antigen Conjugation Systems

Enzyme-labeled antigen has been used for detection of virus-specific antibody. These conjugates are used in antibody capture assays in which an antibody is captured on a solid matrix by an antibody-specific antibody and then subsequently detected by the conjugated antigen (see: U.S. Pat. Nos. 4,273,756 and 4,347,311. This method has been utilized for detecting virus-specific antibody to rubella virus (see: Bonfanti, C., et al, *J. Clin. Micro.* 21:963–968 (1985); cytomegalovirus (see: Schmitz, H. et al. *J. Gen. Virol.* 50:59–68 and Van Loon, A. M., et al, *J. Clin. Micro.* 13:416–422 (1981); Epstein-Barr virus (see: Schmitz, H., *J. Clin. Micro.* 16:361–366 (1982); varicella-zoster virus (see: Sundqvist, V., *J. Virol. Methods* 5:219–227 (1982); and flavivirus (see: Schmitz, H., et al, *J. Clin. Micro.* 19:664–667 (1984)). This method has also been used to detect class-specific and virus-specific antibody to hepatitis virus (see: U.S. Pat. No. 4,273,756).

One disadvantage of the above-described systems is that they cannot detect antigen since they rely solely on antibody capture. A second disadvantage of those systems is that detection of antibody against a single epitope (i.e., antigenic determinant) is difficult because the systems rely upon purified antigen for specificity rather than a monoclonal antibody. A third disadvantage of those systems is that they are not as sensitive as CELISAs.

(V) CELISA and Monoclonal Antibody Conjugate

In the CELISA, the antibody is not captured on the solid matrix by an antibody-specific antibody as in conventional antigen conjugation systems. Instead, an antigen-specific antibody bound to a solid matrix is directly used to capture an antigen-conjugate (see: Voller, A., et al, *The Enzyme-Linked Immunosorbent Assay (ELISA)*, Dynatech Laboratories, Inc. pp. 10–11 (1979) Alexandria, Va.)). The virus antigen is detected by preventing antigen-conjugate binding to the antigen-specific antibody bound to the solid matrix. However, none of the above-described antigen conjugate systems use the CELISA to detect virus-specific antibody. Furthermore, no methods exist for detecting retrovirus core antigen or retrovirus core antigen-specific antibody using a CELISA with or without an antigen conjugate.

A CELISA has been demonstrated for detecting antibody specific for feline infectious peritonitis virus (hereinafter "FIPV") antigens (see: U.S. patent application Ser. No. 716,374, filed Mar. 26, 1985 and Fiscus, S. A., et al, *J. Clin. Micro.* 22:395–401 1985)). This CELISA uses a virus antigen preparation bound to a solid matrix to capture an enzyme-linked monoclonal antibody specific for a single epitope on a single FIPV antigen. Antibody in the test serum is detected by its competition with the conjugated monoclonal antibody for the virus antigen on the solid matrix. Heretofore, this method has not been demonstrated for the detection of retrovirus core antigen and retrovirus core antigen-specific antibody.

SUMMARY OF THE INVENTION

Accordingly, an object of the present invention is to provide a method which can detect either retrovirus core antigen or retrovirus core antigen-specific antibody using the same reagents.

Another object of the present invention is to provide a method that minimizes nonspecific color development in the detection of retrovirus core antigens and retrovirus core antigen-specific antibodies so that false positives are minimal.

A further object of the present invention is to provide a method that identifies only antibody to a single specific epitope on the retrovirus core antigen.

A still further object of the present invention is to provide a method to test for retrovirus core antigen and retrovirus core antigen-specific antibody which is more rapid than existing tests such as the AGID test for EIA.

An additional object of the present invention is to provide a method that is more sensitive than other existing tests, such as the AGID test for EIA, in detecting retrovirus core antigen and retrovirus core antigen-specific antibody.

Another object of the present invention is to provide a method that is easier to interpret results than other existing tests for retrovirus core antigen and retrovirus core antigen-specific antibody, such as the AGID test for EIA.

A further object of the present invention is to provide reagents useful in a method for detecting either retrovirus core antigen or retrovirus core antigen-specific antibody.

In one embodiment of the present invention, the abovedescribed objects have been met by a method for detecting the presence of antibody to retrovirus core antigen, and the presence of retrovirus or retrovirus core antigen comprising: (A) binding a monoclonal antibody specific to retrovirus core antigen to a solid support, (B) reacting the bound monoclonal antibody simultaneously with a labeled retrovirus core antigen and a test sample, (C) removing the unbound test sample and the unbound labeled retrovirus core antigen, and (D) measuring the amount of bound labeled retrovirus core antigen, thereby determining the amount of antibody specific to the retrovirus core antigen and the amount of retrovirus or retrovirus core antigen in the test sample.

In another embodiment of the present invention, the above-described objects have been met by a method for detecting the presence of retrovirus or retrovirus core antigen comprising: (A) binding a monoclonal antibody specific to retrovirus core antigen to a solid support, (B)

reacting the bound monoclonal antibody with a test sample, (C) removing the unbound test sample, (D) reacting labeled retrovirus core antigen with the bound test sample and the monoclonal antibody on the solid support, (E) removing unbound labeled retrovirus core antigen, and (F) measuring the amount of bound labeled retrovirus core antigen, thereby determining the amount of retrovirus or retrovirus core antigen in the test sample.

In still another embodiment, the above objects have been met by a method for detecting the presence of retrovirus or retrovirus core antigen and antibody to retrovirus core antigen comprising: (A) binding retrovirus core antigen to a solid support, (B) reacting the bound retrovirus core antigen simultaneously with a labeled monoclonal antibody specific for retrovirus core antigen and a test sample, (C) removing the unbound test sample and unbound labeled monoclonal antibody, and (D) measuring the amount of bound labeled monoclonal antibody, thereby determining the amount of retrovirus or retrovirus core antigen and antibody specific to the retrovirus core antigen in the test sample.

In a still further embodiment, the above objects have been met by a method for detecting the presence of retrovirus or retrovirus core antigen comprising: (A) binding a monoclonal antibody specific to retrovirus core antigen to a solid support, (B) reacting the bound monoclonal antibody with a test sample, (C) reacting the test sample with a labeled monoclonal antibody specific to the retrovirus core antigen, (D) removing the unbound test sample and unbound labeled monoclonal antibody, and (E) measuring the amount of bound labeled monoclonal antibody, thereby determining the amount of retrovirus or retrovirus core antigen in the test sample.

In an additional embodiment, the above objects have been met by a method for detecting the presence of antibody to retrovirus core antigen comprising: (A) binding retrovirus core antigen to a solid support, (B) reacting the bound retrovirus core antigen with a test sample, (C) removing the unbound test sample, (D) reacting labeled monoclonal antibody specific for retrovirus core antigen with the bound test sample and the retrovirus core antigen on the solid support, (E) removing unbound labeled monoclonal antibody specific for retrovirus core antigen, and (F) measuring the amount of bound labeled monoclonal antibody specific for retrovirus core antigen, thereby determining the amount of antibody specific to the retrovirus core antigen in the test sample.

In another embodiment, the above objects have been met by a hybridoma which produces a monoclonal antibody specific to a retrovirus core antigen and the monoclonal antibody so produced.

DETAILED DESCRIPTION OF THE INVENTION

In some embodiments of the present invention, two components, i.e. (1) a labeled retrovirus core antigen and (2) a monoclonal antibody against the specific retrovirus core antigen, are employed. The use of such an antigen conjugate has not been demonstrated previously for retroviruses. Monoclonal antibodies are employed because polyclonal serum reacts with more than one epitope on the core antigen and thus gives non-specific results.

In other embodiments of the present invention, two other components, i.e. (1) a labeled monoclonal antibody specific for a retrovirus core antigen and (2) retrovirus core antigen are employed. Again, monoclonal antibodies are employed because polyclonal serum will react with more than one epitope on retrovirus core antigen. Heretofore, such a monoclonal antibody has not been developed, i.e., in the present invention, such a monoclonal antibody has been first developed and utilized for the first time.

Retrovirus core antigens can be purified using a variety of procedures such as those disclosed in Shane, B. S., et al, *J. Clin. Micro.* 19:351–355 (1984) and Montelaro, C. J., et al, *J. Virol.* 42:1029–1038 (1982). For example, retrovirus core antigens can be prepared by disrupting retrovirus particles at high temperature or using detergent, followed by HPLC, ion-exchange chromatography, molecular sieve chromatography, differential sedimentation or electrophoresis. The particular procedure employed is not critical so long as it provides a purified preparation of retrovirus core antigen.

The obtained retrovirus core antigen can be used to immunize mice so as to sensitize the spleen cells thereof. These spleen cells are employed as a starting material for producing the hybridomas of the present invention, which produce monoclonal antibodies specific to retrovirus core antigen. The procedures for sensitizing spleen cells are well known in the art (see: Kennett, R. H., McKearn, T. J., and Bechtol, K. B., eds., *Monoclonal Antibodies, Hybridomas: A new dimension in biological analyses*, Plenum Press, Inc., New York, pp. 361–419 (1980)). Further, the procedures for isolating sensitized spleen cells are well known in the art (see: Kennett, R. H., McKearn, T. J., and Bechtol, K. B., eds., *Monoclonal Antibodies, Hybridomas: A new dimension in biological analyses*, Plenum Press, Inc., New York, pp. 361–419 (1980)).

The particular myeloma cell lines employed as starting materials for producing the hybridomas of the present invention, which produce monoclonal antibodies specific to retrovirus core antigen are not critical to the present invention. Examples of such myeloma cell lines include SP2/0 Ag 14 (see: Fiscus, S. A., et al, *J. Clin. Micro.* 22:395–401 (1985)), and FOX-NY (see: Taggert, R. T., et al, *Science* 219:1228–1230 (1983)), P3xG3 Ag8 (see: Kohler, G., et al, *J. Immunol.* 6:292 (1976)), 45.6T61.7. (see: Margulies, D., et al, *Cold Spring Harbor Symp. Quant. Biol.* 41:781 (1977)), WI-L2-729HFZ (see: Strike, L. E., et al, *J. Immunol.* 132:1798 (1984)), MPC-11 (ATCC No. CCL 167), J558 (ATCC No. TIB6), P3.6.2.8.1 (ATCC No. TIB 8), P1.17 (ATCC No. TIB 10), C1.18.4 (ATCC No. TIB 11), RPC5.4 (ATCC No. TIB 12), HOPC1F/12 (ATCC No. TIB 13), RPMI8226 (ATCC No. CCL 155), and ISM2.7 (see: Schuster, J. F., et al, *Human Immunol.* 9:137–143 (1984)).

The production of hybridoma cell lines employing the sensitized spleen cells and well-known myelomas can be performed using well-known procedures (see: Kennett, R. H., *Methods in Enzymology* 58:345–359 (1979), Taggart, R. T., et al, *Science* 219:1228–1230 (1983), Cole, S. P. C., et al, *Mol. Cell. Bioch.* 62:109–120 (1984), Kennett, R. H., McKearn, T. J., and Bechtol, K. B., eds., *Monoclonal Antibodies, Hybridomas: A new dimension in biological analyses*, Plenum Press, Inc., New York (1980)).

The production of a monoclonal antibody specific to retrovirus core antigen is not limited to that obtained from murine hybridomas and can include monoclonal antibodies obtained from human, rat or other animal hybridomas.

The core antigen and antibody specific thereto can be labeled with an enzyme in a CELISA such as horseradish peroxidase (hereinafter "HRPO"), alkaline phosphatase, urease and luciferase by procedures well known in the art. Alternatively, the core antigen and antibody specific thereto can be labeled with a fluorescent marker such as fluorescein, rhodamine, Texas Red (Molecular Probes, Inc.) or ANS (1-anilino-8-naphthalene sulfonate), avidin-biotin or radiolabels such as $^{125}$I, $^{14}$C, $^{32}$P or $^{3}$H by procedures well known in the art.

Enzymes may be conjugated to antibodies or other proteins using any of a variety of coupling reactions. The reaction conditions vary depending upon the exact coupling reagent being used. The coupling reagents include, for example, di-isocyanates, di-aldehydes, carbodiimides, isothiocyanates, mercurics, imidoesters and bismaleimides. These coupling reactions are well known in the art. (see: Kennedy, J. H., et al, *Clin. Chim. Acta* 70:1–31 (1976)).

Many uses of enzyme-conjugated antibodies have been reported. Assays using enzyme-conjugated antibodies range from hormones such as human chorionic gonadotrophin (see: Van Weemen, B. K., et al, *FEBS Letters* 43:215 (1974)) to serum components such as IgE (see: Ericsson, N. E., et al, *Int. Arch. Allergy Appl. Immunol.* 54:88 (1977)) to infectious diseases (see: Holmgren, J., et al, *Infect. Immunity* 7:759 (1977), and Voller, A., et al, *The Enzyme-Linked Immunoabsorbent Assay (ELISA)*, Dynatech Laboratories, Inc. (1979)).

Fluorescent compounds may also be covalently linked to proteins using reagents similar to those employed with enzymes. An example of such a reagent is fluorescene isothiocyanate, wherein the fluorescein group is linked to the isothiocyanate coupling reagent. There are a large number of fluorescent markers available and well known to ones skilled in the art (see: Stryer, L., *Ann. Rev. Bioch.* 47:819–846 (1978), Kennedy, J. H., et al, *Clin. Chim. Acta* 70:1–31 (1976), and Wicker, R., *Ann. N.Y. Acad. Sci.* 177:490–500 (1971)).

Biotinylation of proteins is easily accomplished using the procedure of Goding, J. W., *J. Immunol. Methods* 39:285–308 (1980). Typically, 50–250 μg of biotin succinimide ester is required per milligram of protein. Avidin is coupled to other proteins, such as HRPO. Avidin binds strongly to biotin. Uses for the avidin-biotin system are similar to those listed for enzyme-conjugated antibodies.

Radiolabeled proteins can be obtained using a variety of reagents and labels. Examples of the well-known $^{125}$I labeling kits include Enzymobead radioiodination reagent (Bio-Rad Laboratories) and Iodo-Gen reagent (Pierce Chemicals) (see: Berson, S. A., et al, *J. Clin. Invest.* 35:170–190 (1956) and Skelley, D. S., *Clin. Chem.* 19:146–186 (1973)).

The specific measuring means will depend on the label employed. Such measuring means are well known in the art as exemplified by the above-cited references.

The way to obtain an estimate of the amount of retrovirus present is to measure the test sample relative to a known quantity of standard retrovirus.

Examples of solid supports useful in the present invention include polystyrene or polypropylene microtiter wells; polyethylene, polyvinyl, polypropylene, polycarbonate, polystyrene, or glass test tubes, capillary tubes, dipsticks, or beads; latex beads; nitrocellulose; nylon; cellulose; polyacrilamide; cross-linked dextrans and monocrystalline glass.

Optimal conditions for coating a solid support are best determined by checkerboard titrations using reference reagents. At a minimum, one must test the concentration of antigen or antibody, the time of coating, temperature, buffer conditions and pH. Many antigens can be bound by passive absorption (see: Voller, A., et al, *Manual Clin. Immunol.*, Chap. 69, Amer. Soc. Microbiol. (1976)). Practical aspects are well known to those skilled in the art and guides have been published relative thereto. (see: Voller, A., et al, *The Enzyme-Linked Immunoabsorbent Assay (ELISA)*, pp. 10–11, Dynatech Laboratories (1979)).

The following examples illustrate the present invention and are not intended to limit it in spirit or scope.

EXAMPLE 1

Isolation and Purification of Retrovirus Core Antigen

The Wyoming strain of EIA virus (ATCC No. VR-778 (see: Montelaro, R. C. et al, *J. Virol.* 42:1029–1038 (1982)) was grown using persistently infected fetal equine kidney cells at 37° C. for up to 90 days or until cell senescence using the procedures of Montelaro, R. C., et al, *J. Virol.* 42:1029–1038 (1982). Thereafter, the culture medium was removed and centrifuged at 1000 ×g for 10 minutes. The resulting supernatant was concentrated approximately 50-fold by ultrafiltration using a 100,000 molecular weight cut-off filter. Then, Triton X-100 detergent was added to the supernatant until the final concentration was 0.1% (v/v) (see: U.S. patent application Ser. No. 607,895, filed May 7, 1984). After thorough mixing, the solution was centrifuged in a Beckman L85S ultracentrifuge at 300,000 ×g for 1 hr at 4° C. so that the retrovirus core antigen, i.e. p26, in this instance, remained in the supernatant while other viral proteins were pelleted.

EXAMPLE 2

Sensitization of Spleen Cells

BALB/c mice were injected with up to 50 μg of the core antigen prepared in Example 1 in complete Freund's adjuvant (Difco), intramuscularly, followed by an intraperitoneal boost of up to 50 μg of the core antigen in incomplete Freund's adjuvant (Difco). Seventy-two hours prior to isolation of the spleen cells, up to 25 μg of core antigen in phosphate buffered saline was injected intravenously.

The spleen was removed 3–4 days after the mouse was immunized. The spleen was placed in a 60-mm petri dish in RPMI 1640 medium (Difco) and perfused with medium by injection with a 26-gauge needle at several sites, thereby forcing medium into the spleen. This was continued until most of the spleen cells were removed; the number of spleen cells recovered was usually 5–10×10$^7$ per organ. Care must be taken not to repeatedly draw the suspended cells up into the syringe and force them through the needle (see: Kennett, R. H., McKearn, T. J., and Bechtol, K. B., eds., *Monoclonal Antibodies, Hybridomas: A new dimension in biological analysis*, pp. 361–419, Plenum Press, Inc., New York (1980)).

EXAMPLE 3

Preparation of hybridoma 12E8.1

The spleen cells obtained in Example 2 were fused with SP2/0 Ag 14 myeloma cells (see: Fiscus, S. A., et al, *J. Clin. Micro.* 22:395-401 1985) by using polyethylene glycol 4000.

SP2/0 Ag 14 myeloma cells were grown in RPMI 1640 medium containing 15% (v/v) horse serum seeded at $10^4$ cells per ml for 3-4 days prior to use. The cells were used in an amount of $1 \times 10^5$ to $7 \times 10^5$ cells per ml when they were in the log phase.

The SP2/0 Ag 14 myeloma cells and spleen cells were combined at a ratio of 1:4 and washed three times with RPMI 1640 medium and then centrifuged for 5 min at 1,000 rpm in a 50 ml centrifuge tube. After removing the supernatant, the cell pellet in the bottom of the tube was broken up by external mixing and placed in a 37° C. water bath.

For each $1.6 \times 10^8$ spleen cells employed, 1.0 ml of 50% (w/v) polyethylene glycol 4000 in RPMI 1640 medium and 10 ml of RPMI 1640 medium containing 15% (v/v) fetal calf serum was employed as described below. The polyethylene glycol 4000 was autoclaved at 15 psi for 15 minutes prior to use.

0-1 min—Addition of polyethylene glycol 4000 dropwise with stirring.
1-2 min—Gentle stirring.
2-3 min—1 ml of the RPMI 1640 medium+fetal calf serum was added dropwise with stirring.
3-4 min—1 ml of the RPMI 1640 medium+fetal calf serum was added dropwise with stirring.
4-5 min—3 ml of the RPMI 1640 medium+fetal calf serum was added dropwise with stirring.
5-6 min—The remaining RPMI medium+fetal calf serum was added dropwise with stirring.

Thereafter, the cells were spun for 5 min at 1000 rpm to remove as much of the medium as possible. After washing, the cells were seeded in 96-well microtiter plates at $7.3 \times 10^6$ spleen cells per well in RPMI 1640 medium containing 15% (v/v) fetal bovine serum, 50 units of penicillin per ml, 50 μg of streptomycin per ml and 2 mM L-glutamine. The cultures were fed on days 1, 2, 3 and 4 with the above-described medium supplemented with hypoxanthine ($1.0 \times 10^{-4}$ M), aminopterin ($4.0 \times 10^{-7}$ M) and thymidine ($1.6 \times 10^{-5}$ M). On day 8, the resulting hybridomas were screened for retrovirus core antigen-specific antibody production by an ELISA as described below.

50-100 μl of EIA disrupted virus diluted to 1.0 μg/ml was added to each well. The wells were incubated overnight at 4° C. 100 μl of 1.0% (w/v) BSA in TEN buffer comprising 50 mM Tris, 1 mM EDTA, 150 mM NaCl, pH 7.2 (hereinafter "TEN buffer") was added to each well. This blocking solution was allowed to coat the wells for 1 hr at 37° C. After emptying the contents of the wells, the wells were air dried for up to 1 hr at room temperature. 50-100 82 l of the cell culture supernatant from the hybridoma containing wells was added to the respective ELISA wells. The supernatant was allowed to incubate for 30 min at 37° C. After rinsing the wells, 50-100 μl of secondary antibody (HRPO coupled to goat antimouse antibody (Cappell Laboratories)) at a serial dilution was added to each well. The wells were incubated for 30 min at 37° C. After washing the wells, 50 μl of substrate ABTS solution A (Kirkegaard and Perry Laboratories, Inc.) and 50 μl of substrate ABTS solution B (Kirkegaard and Perry Laboratories, Inc.) was added to each well. The well contents were mixed by gently tapping 10 times. The wells were incubated for 90 minutes at room temperature. The color change was monitored at 405 nm using the Dynatech MR 580 microelisa auto reader. Those wells which scored positive for EIA virus and negative for wells containing the virus negative tissue culture extracts were subcloned as described below.

The ELISA-positive wells were expanded to 2 ml and reassayed, and selected wells were cloned by limiting dilution on BALB/c thymocyte feeder layers until >95% of the colonies from each parent fusion well were positive for antibody specific to retrovirus core antigen. In this manner, hybridoma 12E8.1 was developed. This hybridoma has been deposited at the American Type Culture Collection and received ATCC No. HB-8917.

EXAMPLE 4

Detection of antibodies to EIA virus core antigen using conjugated EIA virus core antigen (A) Preparation of EIA Virus 12E8.1 Monoclonal Antibody Coated Wells The EIA virus 12E8.1 monoclonal antibody, which is a monoclonal antibody against the p26 retrovirus antigen, was purified from ascites fluid-inoculated of Pristane-primed BALB/c mice, intraperitoneally injected with $10^6$ cells of hybridoma 12E8.1 obtained in Example 3 using the following procedures.

The collected ascites fluid was clarified by low-speed centrifugation. Immunoglobulin was precipitated by the addition of saturated ammonium sulfate solution at a final concentration of 43% (w/v). After a thorough mixing and incubation at 4° C. for 2 hours, the solution was centrifuged at 10,000 ×g for 15 minutes at 4° C. The resulting pellet was resuspended in a minimum volume and dialyzed against TEN buffer. The purified monoclonal antibody was diluted to 12 μg/ml with 50 mM Borate pH 8.9. 100 μl was added to each well of a polystyrene microtiter plate. The wells were incubated at 37° C. for 12 hours. After blocking the wells for 1 hour at 37° C. with a 1.0% (w/v) of bovine serum albumin in TEN buffer, the wells were emptied and air dried for 1 hour.

(B) Preparation Of The EIA Virus Core Antigen Conjugate p26 obtained in Example 1 was conjugated to HRPO using the standard procedure described in Nakane, P. K., et al, *J. Histochemistry and Cytochemistry*, 22:1084-1091 (1974). EIA p26 antigen was adjusted to 0.4 mg/ml-1.0 mg/ml with 0.1 M carbonate/bicarbonate buffer, pH 9.6. The antigen was dialyzed against 10 mM carbonate/bicarbonate buffer, pH 9.6, for 18-30 hr. HRPO was dissolved in deionized water up to a concentration of 8-12 mg/ml. Sodium periodate was added to give a final concentration between 160 mM and 200 mM. The HRPO and periodate solution was incubated for 30 min-90 min at 4° C. The solution was then dialyzed against 1.0 mM sodium acetate, pH 4.2, for 6-30 hr. After dialysis, the solution pH was adjusted to 8.5-9.5 with 0.1 M carbonate/bicarbonate buffer, pH 9.6.

The p26 antigen and the thus activated HRPO were mixed so as to achieve final molar ratios of from 15:1 (HRPO:p26) to 5:1 (HRPO:p26). This mixture was incubated for 30 min to 8 hr at 4° C. Ammonium sulfate was then added to a final concentration of 50% (w/v). The precipitate was centrifuged and resuspended in TEN buffer containing 10 mg/ml BSA and 50% (v/v) glycerol. The conjugated EIA virus p26 antigen was stored in 10 mg/ml bovine serum albumin, TEN buffer, 50% (v/v) glycerol at −20° C. until use.

(C) The CELISA Assay

The EIA virus 12E8.1 monoclonal antibody coated wells were filled with 100 μl of sample horse serum. The horse serum was prepared by bleeding a horse with a serum separation tube, allowing it to clot, centrifuging the tube and removing the serum. Then, 50 μl of an 1:1000 dilution of EIA virus p26 antigen conjugate was added to the wells. After mixing the contents of the well by tapping gently 10 times, the assay was incubated for 30 minutes at room temperature. Horse serum which contained antibodies to the EIA virus bound to the conjugated EIA virus antigen and prevented the antigen from binding to the monoclonal antibody bound to the wells. The reagents in the wells were removed and the wells were blotted dry on a paper towel. Then, the wells were flooded with deionized water. The water was then removed. Next, the wash was repeated five times, and the wells were blotted dry on a paper towel after the final rinse. To develop the color reaction, 50 μl of substrate ABTS solution A (Kirkegaard and Perry Laboratories, Inc.) and 50 μl of substrate ABTS solution B (Kirkegaard and Perry Laboratories, Inc.) was added to each well. The well contents were mixed by gently tapping 10 times. The wells were incubated for 90 minutes at room temperature. The color change was monitored at 405 nm using the Dynatech MR 580 microelisa auto reader.

Wells which contained horse serum from EIA negative animals had an $O.D._{405}$ of >1.0. Wells which contained horse serum from EIA positive animals had an $O.D._{405}$ of <0.5.

EXAMPLE 5

Detection of EIA virus core antigen using conjugated EIA virus core antigen (A) Preparation of EIA Virus 12E8.1 Monoclonal Antibody Coated Wells The preparation of EIA virus 12E8.1 monoclonal antibody coated wells was performed as described above in Example 4, Section (A).

(B) Preparation of EIA Virus Antigen Conjugate

The preparation of EIA virus core antigen conjugate was carried out as described above in Example 4, Section (B).

(C) The CELISA Assay

The first row of monoclonal antibody EIA virus 12E8.1 coated wells were filled with 200 μl of horse serum containing up to 200 ng/ml of EIA virus. The remaining wells were filled with 100 μl of EIA virus-negative donor horse serum. 100 μl of serum from the first well was serially diluted (2-fold) into each of the adjacent wells and this was continued across the rows of 2-10 of the microtiter plate. After completing the serial dilutions, the excess 100 μl from row 10 was discarded. Rows 11, 12 contained EIA virus-negative donor horse serum. The wells were incubated at room temperature for 30 minutes. The contents of the wells were removed and the wells were flooded with deionized water. The water was flicked out of the wells and the wash was repeated four times. The wells were patted dry on paper towels. In serum which contained EIA virus core antigen, the core antigen was bound by the monoclonal antibodies in the well, thereby preventing the conjugated EIA virus core antigen from binding to the well.

100 μl of a 1:4000 dilution of HRPO-conjugated EIA virus core antigen in 1.0% (w/v) bovine serum albumin, TEN buffer was added to each well. The wells were incubated at room temperature for 30 minutes. Then, the contents of the wells were discarded and the wells were washed with deionized water. After vigorously flooding the wells, the contents of the wells were removed and the wash was repeated 4 times. Next, the wells were blotted dry on paper towels.

A substrate solution containing 400 μg/ml of o-phenylene diamine in 0.1M citric acid, 0.2M $Na_2HPO_4$, 0.012% (v/v) $H_2O_2$, pH 5.0 was prepared.

100 μl of this substrate was added to each well. The wells were incubated at room temperature for 90 minutes. The substrate reaction was stopped with 50 μl of 2.5N $H_2SO_4$ added to each well. The reaction was read at 490 nm on a Dynatech MR 580 microelisa autoreader.

EIA virus negative donor horse serum provided an $O.D._{490}$ of >1.0. 100 ng/well of EIA virus antigen gave an $O.D._{490}$ of <0.1. The limit of sensitivity of this assay was 250 pg/well of EIA virus.

EXAMPLE 6

Detection of antibody to EIA virus core antigen using conjugated monoclonal antibody specific to EIA virus core antigen (A) Preparation of EIA virus wells EIA virus was grown and disrupted as described in Example 4, Section (B).

100 μl of disrupted EIA virus solution containing 1 μg/ml of protein, which was predominantly p26, in TEN buffer was placed into each well of a microtiter plate. The plate was incubated for 2 hours at 4° C. 100 μl of blocking solution (1.0% (w/v) bovine serum albumin in TEN buffer) was added to each well. The plate was incubated for 1 hour at 37° C. The contents of the wells were removed and the wells were blotted dry on paper towels. The wells were air dried at room temperature for 1 hour.

(B) Preparation of EIA Virus 12E8.1 Monoclonal Antibody Conjugate

The EIA virus 12E8.1 monoclonal antibody was purified from mouse ascites fluid using a 43% (v/v) ammonium sulfate precipitation for 2 hours at 4° C. as described above. The suspension was centrifuged a 10,000 ×g for 15 minutes at 4° C. The resulting pellet was resuspended in a minimum volume and dialyzed against TEN buffer as described above. The purified monoclonal antibody was conjugated to HRPO using the procedure of Tijssen, P., et al, *Anal. Biochem.*, 136:51-457 (1984). More specifically, 12E8.1 monoclonal antibody was adjusted to 5-15 mg/ml with 0.1 M carbonate/bicarbonate buffer, pH 9.6. The antibody was then dialyzed against 10 mM carbonate/bicarbonate buffer, pH 9.6.

Next, HRPO was dissolved in deionized water up to a concentration of 5-30 mg/ml. Sodium periodate was then added to give a final concentration between 1 mM and 100 mM and the HRPO and sodium periodate solution was incubated for 1–18 hr at 4° C.

The antibody and the thus activated HRPO were mixed so as to achieve final molar ratios of from 15:1 (HRPO:Ab) to 5:1 (HRPO:Ab). To this mixture was added ⅓ (w/v) of dry Sephadex G-25 (coarse grade). The resulting mixture was incubated for 3 hr–16 hr at 4° C. The proteins were eluted from the Sephadex G-25 with a minimum volume of carbonate/bicarbonate buffer, pH 9.6. The resulting conjugated monoclonal antibody was precipitated with 50% (w/v) ammonium sulfate, dialyzed against phosphate buffered saline and stored at −20° C. in 1% (w/v) bovine serum albumin and 50% (v/v) glycerol.

(C) The CELISA Assay

The ELISA assay was carried out by placing 50 μl of test horse serum into the wells. 50 μl of HRPO-conjugated EIA virus 12E8.1 conjugated monoclonal antibody was added to the wells. The wells' contents were mixed by gently tapping the well 10 times. The wells were incubated for 30 minutes at room temperature, after which the contents were removed and the wells were flooded with deionized water. The contents of the wells were removed and the wash was repeated 4 times.

To develop the color reaction, 50μl of substrate ABTS solution A and 50 μl of substrate ABTS solution B (Kirkegaard and Perry Laboratories, Inc.) were added to each well. The well contents were mixed by gently tapping 10 times. The wells were incubated from 15–90 minutes at room temperature. The color development was monitored at 405 nm using the Dynatech MR 580 microelisa autoreader.

Wells which contained horse serum from EIA-negative animals had an $O.D._{405}$ of >1.0. Wells which had serum which contained either EIA virus core antigen or antibodies to EIA virus core antigen lowered the signal.

EXAMPLE 7

Detection of EIA virus core antigen using conjugated monoclonal antibody specific to EIA virus core antigen (A) Preparation of EIA Virus 12E8.1 Monoclonal Antibody Coated Wells The wells were prepared as described in Example 4, Section (A).

(B) Preparation of EIA Virus 12E8.1 Monoclonal Antibody Conjugate

HRPO-conjugated monoclonal antibodies specific for EIA virus core antigen were prepared as described in Example 6, Section (B).

(C) The CELISA Assay

The CELISA assay was carried out by placing 50 μl of horse serum containing from 100 pg/ml to 1 μg/ml of EIA virus core antigen into the well. 50 μl of conjugated monoclonal antibody specific for EIA virus core antigen was added to the well. The well contents were mixed by gently tapping the well 10 times. The wells were incubated for 60 minutes at 37° C. The contents of the wells were removed and the wells were flooded with deionized water. After removing the water, the wash was repeated four times.

To develop the color reaction, 100 μl of the o-phenylene diamine substrate, described in Example 5, was added to each of the wells. The wells were incubated at room temperature for 15 minutes. The substrate reaction was stopped by adding 50 μl of 2.5N $H_2SO_4$ to each well. The reaction was read at 490 nm on a Dynatech MR 580 microelisa autoreader.

EIA virus negative donor horse serum provided an $O.D._{490}$ of <0.1. 100 ng of EIA virus provided an $O.D._{490}$ of >1.0. The sensitivity of this assay was <1 ng/well of EIA virus.

While the invention has been described in detail, it will be apparent to one skilled in the art that various changes and modifications can be made therein without departing from the spirit and scope thereof.

We claim:

1. A competition immunoassay for detecting the presence of antibody to Equine Infectious Anemia virus core antigen p26 and also the presence of Equine Infectious Anemia virus or Equine Infectious Anemia virus core antigen p26 comprising:
   (A) binding a monoclonal antibody specific to Equine Infectious Anemia virus core antigen p26 to a solid support,
   (B) reacting the bound monoclonal antibody simultaneously with a labeled Equine Infectious Anemia virus core antigen p26 and a test sample.
   (C) removing the unbound test sample and the unbound labeled Equine Infectious Anemia virus core antigen p26, and
   (D) measuring the amount of bound labeled Equine Infectious Anemia virus core antigen p26, thereby determining the amount of antibody specific to the Equine Infectious Anemia virus core antigen p26 in the test sample and also the amount of Equine Infectious Anemia virus or Equine Infectious Anemia virus core antigen p26 in the test sample.

2. The competition immunoassay according to claim 1, wherein said label is selected from the group consisting of an enzyme, a fluorescent marker, avidin-biotin and a radiolabel.

3. The competition immunoassay according to claim 1, wherein said monoclonal antibody is produced by hybridoma 12E8.1 having the identifying characteristics of ATCC No. HB-8917.

4. The competition immunoassay according to claim 1, wherein said solid support is selected from the group consisting of polystyrene or polypropylene microtiter wells; polyethylene, polypropylene, polycarbonate, polyvinyl, polystyrene, or glass test tubes, capillary tubes, dipsticks, or beads; latex beads; nitrocellulose, nylon; cellulose; polyacrylamide; cross-linked dextrans and microcrystalline glass.

5. A competition immunoassay for detecting the presence of Equine Infectious Anemia virus core antigen p26 comprising:
   (A) binding a monoclonal antibody specific to Equine Infectious Anemia virus core antigen p26 to a solid support,
   (B) reacting the bound monoclonal antibody with a test sample,
   (C) removing the unbound test sample,
   (D) reacting labeled Equine Infectious Anemia virus core antigen p26 with the bound test sample and the monoclonal antibody on the solid support,
   (E) removing unbound labeled Equine Infectious Anemia virus core antigen p26, and
   (F) measuring the amount of bound labeled Equine Infectious Anemia virus core antigen p26, thereby determining the amount of Equine Infectious Anemia virus or Equine Infectious Anemia virus core antigen p26 in the test sample.

6. The competition immunoassay according to claim 5, wherein said label is selected from the group consisting of an enzyme, a fluorescent marker, avidin-biotin and a radiolabel.

7. The competition immunoassay according to claim 5, wherein said monoclonal antibody is produced by hybridoma 12E8.1 having the identifying characteristics of ATCC No. HB-8917.

8. The competition immunoassay according to claim 5, wherein said solid support is selected from the group consisting of polystyrene or polypropylene microtiter wells; polyethylene, polypropylene, polycarbonate, polyvinyl, polystyrene, or glass test tubes, capillary tubes, dipsticks, or beads; latex beads; nitrocellulose; nylon; cellulose; polyacrylamide; cross-linked dextrans and microcrystalline glass.

9. A competition immunoassay for detecting the presence of Equine Infectious Anemia Virus or Equine Infectious Anemia virus core antigen p26 and also the presence of antibody to Equine Infectious Anemia virus core antigen p26 comprising:
   (A) binding Equine Infectious Anemia virus core antigen p26 to a solid support,
   (B) reacting the bound Equine Infectious Anemia virus core antigen p26 simultaneously with labeled monoclonal antibody specific for Equine Infectious Anemia virus core antigen p26 and a test sample,
   (C) removing the unbound test sample and unbound labeled monoclonal antibody,
   (D) measuring the amount of bound labeled monoclonal antibody, thereby determining the amount of Equine Infectious Anemia virus or Equine Infectious Anemia virus core antigen p26 in the test sample and also the amount of antibody specific to Equine Infectious Anemia virus core antigen p26 in the test sample.

10. The competition immunoassay according to claim 9, wherein said label is selected from the group consisting of an enzyme, a fluorescent marker, avidin-biotin and a radiolabel.

11. The competition immunoassay according to claim 9, wherein said monoclonal antibody is produced by hybridoma 12E8.1 having the identifying characteristics of ATCC No. HB-8917.

12. The competition immunoassay according to claim 9, wherein said solid support is selected from the group consisting of polystyrene or polypropylene microtiter wells; polyethylene, polypropylene, polycarbonate, polyvinyl, polystyrene, or glass test tubes, capillary tubes, dipsticks, or beads; latex beads; nitrocellulose; nylon; cellulose; polyacrylamide; cross-linked dextrans and microcrystalline glass.

13. A competition immunoassay for detecting the presence of Equine Infectious Anemia virus or Equine Infectious Anemia virus core antigen p26 comprising:
   (A) binding a monoclonal antibody specific to Equine Infectious Anemia virus core antigen p26 to a solid support,
   (B) reacting the bound monoclonal antibody with a test sample,
   (C) reacting the test sample with a labeled monoclonal antibody specific to the Equine Infectious Anemia virus core antigen p26,
   (D) removing the unbound test sample and unbound labeled monoclonal antibody, and
   (E) measuring the amount of bound labeled monoclonal antibody, thereby determining the amount of Equine Infectious Anemia virus or Equine Infectious Anemia virus core antigen p26 in the test sample.

14. The competition immunoassay according to claim 13, wherein said label is selected from the group consisting of an enzyme, a fluorescent marker, avidin-biotin and a radiolabel.

15. The competition immuinoassay according to claim 13, wherein said monoclonal antibody is produced by hybridoma 12E8.1 having the identifying characteristics of ATCC No. HB-8917.

16. The competition immunoassay according to claim 13, wherein said solid support is selected from the group consisting of polystyrene or polypropylene microtiter wells; polyethylene, polypropylene, polycarbonate, polyvinyl, polystyrene, or glass test tubes, capillary tubes, dipsticks, or beads; latex beads; nitrocellulose; nylon; cellulose; polyacrylamide; cross-linked dextrans and microcrystalline glass.

17. A competition immunoassay for detecting the presence of antibody to Equine Infectious Anemia virus core antigen p26 comprising:
   (A) binding Equine Infectious Anemia virus core antigen p26 to a solid support,
   (B) reacting the bound Equine Infectious Anemia virus core antigen p26 with a test sample,
   (C) removing the unbound test sample,
   (D) reacting labeled monoclonal antibody specific for Equine Infectious Anemia virus core antigen p26 with the bound test sample and the Equine Infectious Anemia virus core antigen p26 on the solid support,
   (E) removing unbound labeled monoclonal antibody specific for Equine Infectious Anemia virus core antigen p26, and
   (F) measuring the amount of bound labeled monoclonal antibody specific for Equine Infectious Anemia virus core antigen p26, thereby determining the amount of antibody specific to the Equine Infectious Anemia virus core antigen p26 in the test sample.

18. The competition immunoassay according to claim 17, wherein said label is selected from the group consisting of an enzyme, a fluorescent marker, avidin-biotin and a radiolabel.

19. The competition immunoassay according to claim 17, wherein said monoclonal antibody is produced by hybridoma 12E8.1 having the identifying characteristics of ATCC No. HB-8917.

20. The competition immunoassay according to claim 17, wherein said solid support is selected from the group consisting of polystyrene or polypropylene microtiter wells; polyethylene, polypropylene, polycarbonate, polyvinyl, polystyrene, or glass test tubes, capillary tubes, dipsticks, or beads; latex beads; nitrocellulose; nylon; cellulose; polyacrylamide; cross-linked dextrans and microcrystalline glass.

21. An immunoassay reagent comprising a solid support coated with a monoclonal antibody specific for Equine Infectious Anemia virus core antigen, p26.

22. The immunoassay reagent according to claim 21, wherein said monoclonal antibody is produced by hybridoma 12E8.1 having the identifying characteristics of ATCC No. HB-8917.

23. The immunoassay reagent according to claim 21, wherein said solid support is selected from the group consisting of polystyrene or polypropylene microtiter wells; polyethylene, polypropylene, polycarbonate, polyvinyl, polystyrene, or glass test tubes, capillary tubes, dipsticks, or beads; latex beads; nitrocellulose; nylon; cellulose; polyacrylamide; cross-linked dextrans and microcrystalline glass.

24. The immunoassay reagent according to claim 21, wherein said monoclonal antibody is labeled.

25. The immunoassay reagent according to claim 24, wherein said label is selected from the group consisting of an enzyme, a fluorescent marker, avidin-biotin and a radiolabel.

26. An immunoassay reagent comprising a solid support coated with Equine Infectious Anemia virus core antigen, p26.

27. The immunoassay reagent according to claim 26, wherein said solid support is selected from the group consisting of polystyrene or polypropylene microtiter wells; polyethylene, polypropylene, polycarbonate, polyvinyl, polystyrene, or glass test tubes, capillary tubes, dipsticks, or beads; latex beads; nitrocellulose; nylon; cellulose; polyacrylamide; cross-linked dextrans and microcrystalline glass.

28. The immunoassay reagent according to claim 26, wherein said monoclonal antibody is labeled.

29. The immunoassay reagent according to claim 25, wherein said label is selected from the group consisting of an enzyme, a fluorescent marker, avidin-biotin and a radiolabel.

* * * * *